United States Patent [19]

Fuisz

[11] Patent Number: 4,997,856

[45] Date of Patent: Mar. 5, 1991

[54] METHOD OF PRODUCING COMPACTED DISPERSABLE SYSTEMS

[75] Inventor: Richard C. Fuisz, Washington, D.C.

[73] Assignee: Fuisz Pharmaceutical Ltd., Washington, D.C.

[21] Appl. No.: 444,045

[22] Filed: Nov. 30, 1989

Related U.S. Application Data

[63] Continuation-in-part of Ser. No. 325,643, Mar. 20, 1989, which is a continuation-in-part of Ser. No. 283,742, Dec. 13, 1988, which is a continuation-in-part of Ser. No. 169,838, Mar. 18, 1988, Pat. No. 4,855,326, which is a continuation-in-part of Ser. No. 169,914, Mar. 18, 1988, Pat. No. 4,873,085, which is a continuation-in-part of Ser. No. 040,371, Apr. 20, 1987, abandoned, said Ser. No. 325,643, is a continuation-in-part of Ser. No. 169,838, , and Ser. No. 169,914, , which is a continuation-in-part of Ser. No. 040,371.

[51] Int. Cl.$^5$ .................. A61K 9/70; A61K 47/00; A61K 31/70; A61L 15/03
[52] U.S. Cl. .................. 514/777; 424/426; 424/439; 424/440; 424/444; 426/517; 426/660
[58] Field of Search ............... 514/777; 424/426, 439, 424/440, 444; 426/517, 660

[56] References Cited

U.S. PATENT DOCUMENTS

| | | | |
|---|---|---|---|
| 3,615,671 | 10/1971 | Shoaf | 426/660 |
| 3,875,300 | 4/1975 | Homm et al. | 424/444 |
| 3,930,043 | 12/1975 | Warning | 426/660 |
| 4,855,326 | 8/1989 | Fuisz | 514/777 |
| 4,873,085 | 10/1989 | Fuisz | 514/777 |

*Primary Examiner*—Shep K. Rose
*Attorney, Agent, or Firm*—Brooks Haidt Haffner & Delahunty

[57] ABSTRACT

Floss spun from a mixture of a saccharide and an oleaginous substance which includes a medicament distributed on or through the fibers is compacted and chopped by passing through a conventional "food grinder" or equivalent having an auger feed to a cutter and orifice plate outlet. The enclosed volume of the end product is less than 30% and preferably less than 15% of the as-spun volume of the floss. This volume reduction is accomplished without distroying the colloidal-like behavior of the product. The compressed particles are readily metered for producing dosage units within required tolerances.

26 Claims, No Drawings

METHOD OF PRODUCING COMPACTED DISPERSABLE SYSTEMS

BACKGROUND OF THE INVENTION

This application is a continuation-in-part of application Ser. No. 07/325,643, filed Mar. 20, 1989, which is a continuation-in-part of application Ser. No. 07/283,742, filed Dec. 13, 1988, which is a continuation-in-part of application Ser. No. 07/169,838, filed Mar. 18, 1988, now U.S. Pat. No. 4,855,326, issued Aug. 8, 1989, which is a continuation-in-part of application Ser. No. 07/040,371, filed Apr. 20, 1987 now abandoned. Application Ser. No. 07/325,643 is also a continuation-in-part of said application Ser. No. 07/169,838, now U.S. Pat. No. 4,855,526 and of application Ser. No. 07/169,914, filed Mar. 18, 1988, now U.S. Pat. No. 4,873,085, issued Oct. 10, 1989, which is another continuation-in-part of application Ser. No. 07/040,371 now abandoned.

In the prior applications preceeding Ser. No. 07/283,742, various substances having pharmacological and or cosmetic properties were combined with a sugar and spun into fibers to produce a readily water-soluble product. The various examples enumerated in those applications involved the use of water soluble medicaments and cosmetic substances and were directed to enhancing the solubility rate of the different substances. As an outgrowth of experimentation with a varied catalog of substances it was discovered that spinning a substance with a sugar can alter the medium in which a particular substance can either dissolve or become dispersed, the latter while forming a colloid or colloidal-like dispersion. Whether or not the dispersions described in the various applications represent true colloidal dispersions or only pseudo-colloidal dispersions, has yet to be determined, although all the evidence seems to favor the conclusion that a true colloid is formed. In any event, when the spun sugar products described in the applications are added to water, the product disperses autogenously throughout the water and remains dispersed. In most instances one observes a general cloudiness associated with a colloidal suspension. But this is not always the case. Several other novel phenomena have been observed also.

The disclosure in application Ser. No. 07/283,742 deals with oleaginous substances such as vegetable oil, baby oil, olive oil, margarine, lanolin, cocoa butter and the like, and how their lack of affinity for water is altered by mixing the oleaginous substance with sugar and melt spinning the mixture in a cotton candy spinning machine or the equivalent. As so modified the products disperse autogenously in water forming a colloidal or colloidal-like dispersion. Such modification enables such widely disparate procedures as: (a) incorporating shortening oil in a cake mix containing flour but no egg to which water is added to produce a batter; and (b) producing a confection or medicated lozenge by dehydrating the dispersion and allowing the melted residue to solidify. It is also disclosed in the −742 application that the addition of an oil additive to the sugar serves to stabilize the resultant floss increasing its shelf life significantly.

All of the prior applications dealt essentially with an expanding universe of products. However, the general procedure for producing the products was initially set forth in the earliest applications, namely those that resulted in U.S. Pat. No. 4,855,326. Referring to that patent, it is stated therein that in order to convert the cotton-like mass, i.e., the mass of spun fibers, to a form that can be packaged and handled, the as-spun product generally must be compacted to produce a compact body being careful not to squeeze too much. The following is quoted from the patent. "It is important that the final dosage form retains its fibrous character so that it will dissolve rapidly in the saliva of the mouth or other solvent. At present, it is believed desirable for tablet production to reduce the initial spun volume by approximately two thirds or until the threshold is reached beyond which the fibers would fracture or coalesce. Preferably, the material is compacted as much as possible to produce a wafer-like structure while avoiding fracturing of the fibers or loss of the discrete fibrous identity. However, it will become apparent from the ensuing description that there will be occasions when a lesser degree of compaction or even no compaction is desirable. When compaction is employed, it preferably is performed to produce a body with an enclosed volume that is at least 30% less than the as-spun enclosed volume." It was contemplated in said patent that initial partial compaction could be achieved by passing the floss between rollers or the like to produce a fibrous web which would be further compacted by pressure from the enveloping packaging material. The emphasis was placed throughout said patent, however, on not compressing the fibrous mass to the point of destroying its fibrous structure.

In the manufacture of pharmaceuticals it is imperative that dosage units contain a known quantity of the involved medicament and that the controls be such that dosage units can be produced all with the same quantity of the given medicament within quite stringent tolerance limits. Heretofore, it was believed that the fibrous material could not be compressed much more than to two thirds its initial spun volume. While this produced a compacted web that could be packaged and severed, difficulty was encountered in controlling the density of the compacted material and it was so light in weight that existing weighing devices were not sufficiently sensitive to effect necessary control.

SUMMARY OF THE PRESENT INVENTION

It is, therefore, an object of the present invention to provide a method for producing a floss form of a pharmaceutical product that has sufficient weight-to-volume ratio to enable production of controlled dosage units at reasonable production rates.

It is another object of the present invention to provide a method for compacting a mass of spun saccharide fibers to less than ⅓ its initial spun volume while not destroying said fibers or the ability of said mass to disperse rapidly in water.

Other objects will occur to those skilled in the subject art after reading the detailed description.

In accordance with one aspect of the present invention there is provided a method for converting a fluffy mass of spun fibers into a product capable of being readily subdivided into any desired predetermined quantity where said fibers include at least one saccharide, and at least one oleaginous substance is distributed on or incorporated in said fibrous mass, said method comprising compacting said fluffy mass of fibers to produce a compacted product having an enclosed volume less than 30% of the as-spun enclosed volume of the original fluffy mass.

In accordance with another aspect of the present invention there is provided a method for preparing a stable pharmaceutical product for delivering a medicament, comprising in combination the steps of producing a mixture containing a medicament by at least combining an oleaginous substance with a saccharide capable of being spun into fibers that are readily water-soluble, processing said mixture to yield a fluffy mass of spun fibers, thereafter compacting said fluffy mass of fibers to produce a compacted product having an enclosed volume less than 30% of said as-spun enclosed volume.

The invention will be better understood after reading the following detailed description of the presently preferred embodiments thereof.

DETAILED DESCRIPTION OF THE PRESENTLY PREFERRED EMBODIMENTS

U.S. Pat. No. 4,855,326 describes methods for combining a medicament with any one or more of the water soluble melt spinnable sugars and spinning the combination to produce a readily soluble floss form of the medicament. The disclosure of such patent is incorporated herein by reference.

Co-pending application Ser. No. 07/283,742 discloses that any oleaginous substance that can be mixed with a melt-spinnable sugar, when spun in a cotton candy spinning machine, produces a product which, when added to water or has water added to it, forms, virtually autogenously, a uniform dispersion having all the appearances of a colloidal dispersion. All of the examples included in said application Ser. No. 07/283,742 assumed addition of the fibrous product to water at normal room temperature. The disclosure of such application is incorporated herein by reference.

U.S. Pat. No. 4,873,085 discloses methods for combining a cosmetologically effective substance with any one or more of the water soluble melt spinnable sugars and spinning the combination to produce a readily soluble floss form of the cosmetologic substance. The disclosure of such patent is incorporated herein by reference.

Co-pending application Ser. No. 07/325,643 discloses that a spun product from a combination of a saccharide and a hydrophobic ingredient is hydrophillic with low concentrations of such ingredient but becomes increasingly hydrophobic as the concentration of the hydrophobic ingredient is increased, although the end product nevertheless acts hydrophilically when the water temperature is elevated. Larger ratios of hydrophobic substance-to-saccharide yields a spun fibrous product that has increased stability. Similar stabilization can be attained by adding either beeswax or a petrolatum to the saccharide either in the presence of or absence of a separate active ingredient. Examples are given for masking the taste of unpalatable medicaments or other ingestible substances. Delayed release burn or wound dressings are also described. Control with beeswax can also provide a time release tablet or the like when swallowed. The disclosure of such application is incorporated herein by reference.

The fiberous product as produced by any of the methods described in the various above-mentioned patents and applications, in its as-spun condition, must be compacted to produce a weight-to-volume ratio that is susceptible of accurate measurement by automated production machinery. It has now been discovered that any of the oleaginous containing fibrous masses produced by the prior methods can be compacted in a conventional industrial meat grinder or its equivalent without destroying the colloidal-like nature of the product. The invention can best be described and understood from a consideration of a few examples.

For the following examples the floss spinning machine used was: Econo floss Model 3017 manufactured by Gold Medal Products Co. of Cincinnati, Ohio. Unless otherwise stated, reference to sucrose in the examples is to "Gold Medal" flossugar, Jolly Berry flavor. Unless otherwise indicated, the temperature of the grid in the spinning machine was about 180° F. (82.2° C.) while the operating speed was about 3800 R.P.M.

EXAMPLE I

Using a "KitchenAid" Proline Model KSM5 mixer with metal wisk attachment, 3 lbs. of Town House Fine granulated sugar (sucrose) was blended, with soy oil in the volume ratio of 3 parts sugar to 1 part oil, at high speed for about 5 minutes. The mix was then spun in the floss spinning machine at the heat setting normally used for the sucrose alone.

Next, the wisk attachment was replaced with a "KitchenAid" Food Grinder attachment, Model FG-A having a plastic sleeve and hopper, a metal auger, a metal multi-arm cutter, and a series of aperture plates with different size and number of apertures. The floss produced by spinning was fed to the hopper of the grinder and pressed down onto the auger with a conventional wooden plunger. Chopped floss exited the grinder and was collected in a container. It was considerably denser than any floss previously prepared. A 1 quart container held 2 to 3 lbs of compacted particulate floss. Substantially all of the floss was processed through the grinder which was operating at a speed of approximately 40 R.P.M. with an orifice plate at its outlet having eight apertures, each of 5/16" diameter.

EXAMPLE II

Example I was repeated for each of the following sugar and oil combinations with all conditions being the same and with essentially the same results.

| SUGAR | OIL |
| --- | --- |
| SUCROSE | CORN |
| SUCROSE | OLIVE |
| *DEXTROSE | SOY |
| *DEXTROSE | CORN |
| *DEXTROSE | OLIVE |

*The dextrose was obtained from Sigma Chemical Co. of St. Louis, Missouri.

EXAMPLE III

Starting with 1 cup of sucrose (flossugar from "Gold Medal") and 1 tsp. Crisco vegetable oil, the ingredients were mixed with a spoon to blend and spun with the floss machine. The yield was approximately 22 cups of floss with very slight compaction, say about 10%. This quantity of floss was then passed through the "KitchenAid" grinder and yielded about 3 cups of chopped particles for a volume reduction of about 86%.

EXAMPLE IV

A quantity of each of the products produced in Examples I and II was added to water at room temperature. In every instance the solids dispersed colloidal-like.

EXAMPLE V

Using "Safeway" granulated sugar and soy oil, in the volume ratio of 3 parts sugar to 2 part oil, a quantity of floss was prepared by blending the ingredients and spinning with the floss machine.

Using the food grinder of Example I, the floss was processed at varying auger speeds and with different size orifice plates. It was found that an auger speed of 40 R.P.M. with the orifice plate having eight 5/16" diameter apertures produced several quarts of particulate floss with no jam up during in excess of 1 hour of operation. Attempts to increase auger speed over 50 R.P.M. were met with the grinder jamming within a minute of such operation. The temperature of the auger became extremely high. Any attempt to use an orifice plate with smaller holes also resulted in stalling the grinder within about 1 minute of operation.

From the foregoing examples it has been concluded that the spun floss can be compacted in an efficient manner on a continuous basis so long as working the floss mass does not overheat the floss and cause the sugar content to become so tacky as to begin to coalesce and to stick to the walls of the apparatus and jam up. The colloidal-like behavior of the product does not appear to be destroyed by the compacting action of the auger and cutter of the grinder. Yet, a particulate product is produced that has substantially greater density than the as-spun floss, and which can be weighed and metered out with reasonable accuracy.

It is to be understood that any of the pharmaceutical products produced in floss form by methods described in the above-mentioned prior applications and patents, which products have an oleaginous content, can be processed through an auger type compactor similar to the grinder used in the Examples herein to reduce the enclosed volume of the product to less than 30% of the as-spun enclosed volume, and preferably to less than 15% of the as-spun enclosed volume. Also, it should be understood that the cutter blade of the grinder serves to break up the compacted product into discrete particles. The particulate output of the grinder is readily metered out into discrete predetermined volume or weight size dosage units.

Having described the present invention with reference to the presently preferred embodiments thereof, it will be apparent to those skilled in the subject art that various changes and modifications can be incorporated without departing from the true spirit of the invention as defined in the appended claims.

What is claimed is:

1. A method for preparing a stable pharmaceutical product for delivering a medicament comprising in combination the steps of producing a mixture containing a medicament by at least combining an oleaginous substance with a saccharide capable of being spun into fibers that are readily watersoluble, processing said mixture to yield a fluffy mass of spun fibers, thereafter compacting said fluffy mass of fibers to produce a compacted product having an enclosed volume less than 30% of said as-spun enclosed volume.

2. A method according to claim 1, comprising the further step of breaking up said compacted product into a quantity of discrete particles.

3. A method according to claim 2, comprising the further step of subdividing said quantity of discrete particles into discrete predetermined dosage units.

4. A method according to claim 1, comprising the further step of subdividing said compacted product into discrete predetermined dosage units.

5. A method according to claim 1, wherein said compacting step is performed by feeding said fluffy mass of fibers into a cylinder containing a rotatable auger and an outlet provided with orifice means, and rotating said auger to compact the fibers and express the compacted fibers through said orifice means.

6. A method according to claim 5, wherein the speed of rotation of said auger and the size of the openings in said orifice means are maintained and related to compress and express the fluffy mass without raising the temperature of the fibers above a critical temperature at which the material of said fluffy mass would commence to coalesce.

7. A method according to claim 6, comprising the further step of breaking up said compacted product into a quantity of discrete particles.

8. A method according to claim 7, comprising the further step of subdividing said quantity of discrete particles into discrete predetermined dosage units.

9. A method according to claim 6, comprising the further step of subdividing said compacted product into discrete predetermined dosage units.

10. A method according to claim 1, wherein said compacted product is produced with an enclosed volume that is less than 15% of said as-spun enclosed volume.

11. A method according to claim 10, comprising the further step of breaking up said compacted product into a quantity of discrete particles.

12. A method according to claim 11, comprising the further step of subdividing said quantity of discrete particles into discrete predetermined dosage units.

13. A method according to claim 10, comprising the further step of subdividing said compacted product into discrete predetermined dosage units.

14. A method according to claim 10, wherein said compacting step is performed by feeding said fluffy mass of fibers into a cylinder containing a rotatable auger and an outlet provided with orifice means, and rotating said auger to compact the fibers and express the compacted fibers through said orifice means.

15. A method according to claim 14, wherein the speed of rotation of said auger and the size of the openings in said orifice means are maintained and related to compress and express the fluffy mass without raising the temperature of the fibers above a critical temperature at which the material of said fluffy mass would commence to coalesce.

16. A method according to claim 15, comprising the further step of breaking up said compacted product into a quantity of discrete particles.

17. A method according to claim 16, comprising the further step of subdividing said quantity of discrete particles into discrete predetermined dosage units.

18. A method according to claim 15, comprising the further step of subdividing said compacted product into discrete predetermined dosage units.

19. A method for converting a fluffy mass of spun fibers into a product capable of being readily subdivided into any desired predetermined quantity where said fibers include at least one saccharide, and at least one oleaginous substance is distributed on or incorporated in said fibrous mass, said method comprising compacting said fluffy mass of fibers to produce a compacted product having an enclosed volume less than 30% of the as-spun enclosed volume of the original fluffy mass.

20. A method according to claim 19, comprising the further step of breaking up said compacted product into a quantity of discrete particles.

21. A method according to claim 19, wherein said compacting step is performed by feeding said fluffy mass of fibers into a cylinder containing a rotatable auger and an outlet provided with orifice means, and rotating said auger to compact the fibers and express the compacted fibers through said orifice means.

22. A method according to claim 21, wherein the speed of rotation of said auger and the size of the openings in said orifice means are maintained and related to compress and express the fluffy mass without raising the temperature of the fibers above a critical temperature at which the material of said fluffy mass would commence to coalesce.

23. A method according to claim 19, wherein said compacted product is produced with an enclosed volume that is less than 15% of said as-spun enclosed volume.

24. A method according to claim 19, wherein said mass of spun fibers is produced by melt spinning a mixture of said saccharide and said oleaginous substance where said mixture includes a medicament.

25. A method according to claim 24, wherein said saccharide is selected from the group consisting of sucrose, lactose, dextrose and combinations thereof.

26. A method according to claim 25, wherein said oleaginous substance is a vegetable oil.

* * * * *